(12) United States Patent
Wickramasinghe

(10) Patent No.: US 9,255,290 B2
(45) Date of Patent: Feb. 9, 2016

(54) METHODS AND DEVICES FOR NON-THERMAN POLYMERASE CHAIN REACTION

(71) Applicant: The Regents of the University of California, Oakland, CA (US)

(72) Inventor: Hemantha Kumar Wickramasinghe, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/830,397

(22) Filed: Mar. 14, 2013

(65) Prior Publication Data

US 2014/0273099 A1  Sep. 18, 2014

(51) Int. Cl.
| | | |
|---|---|---|
| *C12Q 1/68* | (2006.01) | |
| *C07H 21/02* | (2006.01) | |
| *C07H 21/04* | (2006.01) | |

(52) U.S. Cl.
CPC ..................................... *C12Q 1/686* (2013.01)

(58) Field of Classification Search
CPC .......................... C12Q 1/686; C12Q 2523/307
See application file for complete search history.

(56) References Cited

U.S. PATENT DOCUMENTS

| | | | |
|---|---|---|---|
| 4,683,195 A | | 7/1987 | Mullis et al. |
| 4,683,202 A | | 7/1987 | Mullis |
| 6,051,380 A | * | 4/2000 | Sosnowski et al. .......... 435/6.11 |
| 6,333,157 B1 | * | 12/2001 | Miller-Jones et al. ....... 435/6.19 |
| 6,365,400 B1 | | 4/2002 | Stanley |
| 6,372,484 B1 | | 4/2002 | Ronchi et al. |
| 7,537,917 B2 | | 5/2009 | Collins |
| 2002/0172969 A1 | * | 11/2002 | Burns et al. ....................... 435/6 |
| 2003/0104466 A1 | | 6/2003 | Knapp et al. |
| 2008/0020380 A1 | | 1/2008 | Patno et al. |
| 2011/0212492 A1 | | 9/2011 | Hirahara |

OTHER PUBLICATIONS

Karami, A. et al., J. Global Infect. Dis., vol. 3, pp. 293-302 (2011).*
Innis et al. , PCR Protocols: A Guide to Methods and Applications, pp. 3-12 (1990).*
Westin, L. et al., Nature Biotechnol., vol. 18, pp. 199-204, 2000).*

* cited by examiner

*Primary Examiner* — Teresa E Strzelecka
(74) *Attorney, Agent, or Firm* — Robert D. Buyan; Stout, Uxa & Buyan, LLP

(57) ABSTRACT

Methods and devices for non-thermal PCR amplification of nucleic acid sequences. An electrical potential is applied to cause non-thermal separation of strands of a double-stranded nucleic acid or double-stranded nucleic acid/primer extension product.

14 Claims, 7 Drawing Sheets

METHODS AND DEVICES FOR NON-THERMAN POLYMERASE CHAIN REACTION

FIELD OF THE INVENTION

The present invention relates generally to methods and devices useable for analysis of deoxyribonucleic acid (DNA) and more particularly to devices and methods for denaturing nucleic acid products such as during performance of a polymerase chain reaction (PCR) analysis.

BACKGROUND OF THE INVENTION

Pursuant to 37 CFR 1.71(e), this patent document contains material which is subject to copyright protection. The copyright owner has no objection to facsimile reproduction of the entire patent document or the patent disclosure, as it appears in the Patent and Trademark Office patent file or records, but otherwise reserves all copyright rights whatsoever.

Deoxyribonucleic acid (DNA) molecules carry the genetic code that determines many physical and functional characteristics of organisms. Each DNA molecule consists of two helical backbones or "strands." The helical strands are bound to each other to form a double helix. Each DNA strand is made up of four types of nucleotide bases, namely, adenine, guanine, thiamine and cytosine. The nucleotide bases on one strand form geometrically specific bonds (hydrogen bonds) with nucleotide the same type on the adjacent strand. Thus, the bases bond in type-specific pairs, i.e., adenine to adenine, guanine to guanine, etc. If the strands are subsequently separated, each strand provides a pattern of successive bases that can be used as a template for reconstruction of a DNA molecule that is the same as the original DNA molecule. This process occurs naturally in living organisms and is known as "replication."

Modern DNA analysis techniques are frequently used to identify, match or characterize DNA by determining the specific nucleotide sequence that exists in DNA sample. However, sometimes, the available DNA sample is relatively small—such as when the DNA originates from a microorganism or tiny drop of body fluid found at a crime scene. When the available DNA sample is small, it is necessary to amplify the DNA from the sample. This amplification is performed by a laboratory technique that, in many respects, mimics natural DNA replication. This laboratory technique is known as "polymerase chain reaction" (PCR). U.S. Pat. Nos. 4,683,202 and 4,683,195 describe basic PCR technology and the entire disclosures of both such patents are expressly incorporated herein by reference.

PCR is typically carried out in cycles, with each cycle consisting of three steps, namely denaturation, annealing and extension. Prior to the denaturation step, a sample mixture is typically prepared which contains the DNA (or a quantity of body fluid or tissue that is believed to contain the DNA), primers and enzyme(s).

During the denaturation step, all or substantially all (e.g., 99%) of the DNA double helix is separated into two individual complimentary strands. This has heretofore been done by heating a DNA sample mixture to a temperature of between about 90 and 105 degrees C. for a period of between about one and ten minutes. This elevated temperature causes thermal separation of the DNA double. In some applications, this increase in temperature can also serve to terminate chemical reactions which had begun within the sample during a previous cycle.

In the annealing step, the specific oligonucleotide primers are attached to the DNA strands. Primers are needed because the DNA enzymes cannot start DNA chains from scratch. Instead, the primer is required to determine the location along a particular DNA template at which the synthesis of the complementary strand will begin. This allows the technique to be used to amplify a particular target region of DNA by selection of primers that are specific to that target region. In essence, each primer is a synthetic segment of single-stranded DNA that contains about 20-30 bases and a chemical label which allows it to be located and identified. In most PCR procedures, two primers are used, one for each of the complementary single DNA strands produced during the denaturation step. The annealing step is typically accomplished by lowering the temperature to between about 50 and 60.degrees C. This causes the primers to attach to the individual DNA strands.

Once the annealing step has caused the primers to bind to the DNA strands, the temperature is again raised, typically to greater than 70 degrees C., causing the enzyme(s) to activate. This activation of the enzyme(s) causes replication of the DNA strands. More specifically, the enzyme(s) synthesizes new double-stranded DNA molecules by facilitating the joining of complementary nucleotides (i.e., the sugar joined to a base and to a phosphate group) in the sample mixture.

As a result, at the end of the first PCR cycle, two new DNA strands are present, each of which is identical to the original target DNA strand that was denatured and primed. Typically, about 30 of these thermal PCR cycles are required to provide a sufficient amount of DNA for analysis. This can be quite time consuming. For example, each thermal denaturation step can take about two minutes. Each annealing step can also take about two minutes. Then, each extension step can also take about two minutes. As a result, the thermal cycling in each PCR cycle may takes about six minutes and a full 30 cycle PCR amplification can take about 3 hours.

Moreover, in thermal PCR, if the temperatures and times of the cycles are not precisely controlled, the desired amplification may not be achieved. Furthermore, because thermal denaturing requires relatively high temperature, the enzyme(s) in the DNA sample mixture must be selected from a limited number of enzymes that remain stable at these elevated denaturation temperatures or, alternatively, additional enzyme must be added after each PCR cycle. In this regard, Taq polymerase is the enzyme frequently used in thermal PCR because it remains stable and does not break down at the DNA denaturation temperatures. However, high temperature enzymes such as Taq lack capabilities that may be available with other less temperature-stable enzymes. For example, Taq polymerase lacks a 3' to 5' exonuclease activity which, if present, allows the enzyme to identify misplaced bases and replace them with correct bases in the correct positions. The use of an enzyme that has 3' to 5' exonuclease activity can avoid potentially undesirable amplification of errors in the target sequence.

Also, thermal PCR is routinely limited to target sequences within a certain size range—e.g., between about 2000 and 3000 base pairs. The use of thermal PCR for amplification of larger targets (e.g., up to 50,000 base pairs) can require very long heating cycles and special enzymes that may not be stable in such long heating cycles.

PCR amplification has a wide range of clinical and investigational applications. For example, in subjects who are infected with a specific microorganism (e.g., a virus, bacterium, fungus, etc.), a sample of body fluid or tissue may contain such a small amount the infecting organism's DNA that direct identification of the organism's DNA is difficult or impossible. However, PCR can be used to amplify the infecting organism's DNA to provide an amount that can be easily analyzed and identified. For this reason, PCR is used in a number of diagnostic tests for infectious diseases. Additionally, in some instances, PCR techniques can be used to not only determine that a particular organism is present but to also quantify how much of the infecting organism is present in the fluid or tissue sample. Such quantification can be valuable in assessing the severity of the infection and/or the efficacy of an ongoing treatment (e.g., periodic measurement of viral load in individuals receiving antiviral therapy).

PCR is also used to facilitate testing and screening of donated blood for the presence of presence of even very low levels of infectious organisms (e.g., Hepatitis B virus (HBV); Hepatitis C virus (HCV 3.0); Human Immunodeficiency viruses Types 1 and 2 (HIV 1,2); Human T-Lymphotropic virus (HTLV-I/II); Syphilis (*Treponema pallidum*); West Nile virus (WNV) and Chagas disease (*T. cruzi*)

Moreover, PCR can be used in genetic counseling. For example, PCR techniques can be used to analyze small samples of a subject's blood for the presence or absence of certain genes (e.g., certain specific nucleic acid sequences), thereby indicating whether that subject is predisposed toward a particular disease or condition and/or predicting how that subject may respond to a particular drug or biologic treatment.

Additionally, PCR amplification has also been used to purify a DNA-containing sample or material. In such applications, PCR amplification is used to increase the amount of DNA in the sample or material until the proportional amount of the DNA in the sample or material far exceeds the amounts of contaminants, thus effectively reducing the proportional amounts of the contaminants to trivial levels.

Also, PCR amplification can also be used to create DNA libraries that are useable in conjunction with combinatorial chemistry techniques, for various clinical and investigational purposes.

In view of the wide range of potential applications for PCR amplification techniques and the inherent limitations and drawbacks associated with thermal PCR, the prior art has included various methods and devices which purportedly eliminate the need for thermal cycling during PCR or, at least, provide for faster thermal cycling to limit the time required for the process.

For example, United Kingdom Patent Application Publication No. GB2,247,880 (Stanley) describes non-thermal methods and apparatus for converting a double stranded nucleic acid to a denatured single stranded nucleic acid by applying an electric potential to a solution containing the nucleic acid. The described process may be carried out at ambient or near ambient temperature. The strand separation comes about by electron transfer to DNA that is free in the solution and adsorbed onto an electrode. In the examples provided, the solution containing the DNA also contains a mediator which receives electrons from the electrode and transfers them to the DNA to effect said strand separation. Such mediator is defined as "an inorganic or organic molecule which is capable of reversible electron transfer at an electrode and which passes electrons on to or receives electrons from a biological molecule, in this instance the nucleic acid present in solution." It is further stated that the mediator "should be soluble in the solvent for the DNA (which may be water or a solvent other than water) and compounds having a redox potential of 0 to −2 volts, 25 preferably −0.2 to −1 volt and especially about −0.4 volts are preferred. Thus the mediator may be a water or solvent soluble compound having conjugated or aromatic groups and one or more hetero-atoms and may be a compound of the quinone or bipyridyl series, especially a viologen such as 5 methyl viologen or a salt thereof. The choice of mediator is not believed to be critical provided that its redox potential is within the required voltage range and compound does not otherwise affect or interfere with DNA or other materials present in 10 the solution such as enzymes or oligonucleotide probes. The use of a mediator enables the DNA or other nucleic acid material to be denatured into its individual strands at an applied voltage of −0.1 volt or less. Although denaturation has been observed by the present inventors at a voltage of −1 volt, it is believed that this may be an overvoltage and the voltage needed to bring about actual denaturation may be as low as −0.8 volts especially since the redox potential of the mediator is 20 typically 0.4 volts." In some embodiments, the process may be carried out using a modified electrode "in which the electron transfer is e.g. by an electron donating or electron accepting compound such as a mediator coated onto, or adsorbed onto, the surface of the electrode which is otherwise of an inert material." Or, "[t]he electron transfer may also be from or to an electrode consisting at least partially of a mediator compound e.g. formed wholly of the mediator compound."

U.S. Pat. No. 6,365,400 (Stanley) describes a process for denaturing double-stranded nucleic acid material into its individual strands using an electrochemical cell. This process is an electrical treatment of the nucleic acid with a voltage applied to the nucleic acid material by an electrode. This process may be used in the detection of nucleic acid by hybridizing with a labeled probe or in the amplification of DNA by a polymerase chain reaction or ligase chain reaction. The process may also employ a promoter compound, such as methyl viologen, to speed denaturation.

PCT International Patent Publication WO9802573 (Purvis) also describes non-thermal methods and apparatus for converting a double stranded nucleic acid to a denatured single stranded nucleic acid by applying an electric potential to a solution containing the nucleic acid. An effective concentration of Lithium ions are added to the sample to act as a promoter of the denaturation.

United States Patent Application Publication No. 2011/0212492 (Hirahara) describes methods and devices wherein a PCR reaction solution is passed between electrodes and low voltage electrical current is passed through the reaction solution to generate sufficient Joule heat for the PCR cycle without electrolyzing the reaction solution. This method does use thermal cycling. The low voltage electrical current is merely used to precisely control the heating of the reaction solution.

Others have described the use of ultrasonic energy, rather than thermal cycling, in PCR. Specifically, United States Patent Application Publication No. 2008/002038 (Patno, et al.) describes a method and apparatus for processing a DNA or RNA sample within a sample processing module. The method includes the steps of providing a sample well within the sample processing module that contains the DNA or RNA sample, coupling ultrasonic energy from an external source into the sampling well and denaturing and fragmenting the DNA or RNA sample using the ultrasonic energy.

Also, microwave assistance has been described as a means for reducing the amount of thermal cycling required during a PCR process. Specifically, U.S. Pat. No. 7,537,917 describes a method of microwave assisted nucleic acid amplification by PCR in which at least the denaturing and extension steps are carried out under the influence of microwave radiation, while preventing the temperature of the sample from varying more than 40° C. from start to finish, and while maintaining the temperature of the sample from start to finish at no more than 60° C.

Additionally, United States Patent Application Publication No. 2003/0104466 (Knapp et al.) describes a non-thermal polymerase chain reaction method that is performed using a microfluidic device. The microfluidic device has a reaction chamber or channel that contains a target nucleic acid sequence and primer sequences, a source of a chemical denaturant and a source of polymerase enzyme fluidly connected to the reaction chamber or channel and a fluid direction system for delivering the chemical denaturant or the polymerase enzyme to the reaction chamber or channel. Complementary strands of the target nucleic acid sequence are "melted" by delivering a volume of the chemical denaturant to the reaction chamber or channel. The primer sequences are annealed to the target nucleic acid by eliminating a denaturing effect of the chemical denaturant. The primer sequences are then extended along the target nucleic acid sequence by delivering a volume of the polymerase enzyme to the reaction chamber or channel. These steps of melting, annealing and extending are repeated to amplify the target nucleic acid sequence.

The entire disclosure of each of the above-cited patents and published patent applications is expressly incorporated herein by reference.

There remains a need in the art for the development of further alternatives and improvements to the PCR and nucleic acid amplification techniques of the prior art to lessen the time required and/or the complexity of the process.

SUMMARY OF THE INVENTIONS

The present invention provides methods and devices for non-thermal PCR amplification of nucleic acid sequences as described herebelow and as shown in the accompanying drawings.

In general, the present invention provides methods and devices for separating the strands of a double-stranded nucleic acid or double-stranded nucleic acid/primer extension product by applying an electrical potential to cause non-thermal separation of strands of the double-stranded nucleic acid or double-stranded nucleic acid/primer extension product, wherein the electrical potential is applied in the substantial absence of lithium ions or any initiator or promoter substance that a) receives electrons from an electrode and transfers them to the double-stranded nucleic acid or double-stranded nucleic acid primer extension product and b) has a redox potential of 0 to −2 volts.

In some embodiments, the present invention is used to accomplish the denaturation step of a PCR process by voltage cycling rather than thermal cycling. The voltage cycling PCR process of the present invention is sometimes referred to herein by the acronym "vcPCR." In some applications of vcPCR, the electrical potential is created between two electrodes and one or more oligonucleotide primers is/are attached to a substrate that comprises or is situated close to an electrode, thereby facilitating the process of the present invention.

Further aspects, details and examples of the present inventions will be understood upon reading of the detailed description and examples set forth herebelow.

BRIEF DESCRIPTION OF THE DRAWINGS

The following detailed description and examples are provided for the purpose of non-exhaustively describing some, but not necessarily all, examples or embodiments of the invention, and shall not limit the scope of the invention in any way.

FIG. 3 (Panels 1 through 8) are schematic diagrams showing steps in a prior art method for DNA analysis by solid state bridge amplification in a flow cell.

DETAILED DESCRIPTION OF THE INVENTION

The following detailed description and the accompanying drawings to which it refers are intended to describe some, but not necessarily all, examples or embodiments of the invention. The described examples or embodiments are to be considered, in all respects, as illustrative but not restrictive. The contents of this detailed description and the accompanying drawings do not limit the scope of the invention in any way.

The vcPCR methods of the present invention include various embodiments. For example, described below are vcPCR Bridge Amplification and vcPCR Solid Phase Amplification Using a Single Forward Primer. Also described below are examples of some devices that may be used for performing vcPCR in accordance with the methods of the present invention. In the examples described below, vcPCR may rely generally on the following features:

1) At least one of the primers (forward or reverse) is attached (e.g., by its 5' end) onto a first electrode (e.g., a "base electrode").
2) A second electrode (e.g., a counter-electrode) is positioned close enough to the first electrode to apply a denaturing electrical potential (e.g., a "melting field") across the nucleic acid being denatured.

It has been reported that 65 pN is the critical force at which double stranded DNA denatures (or melts) in a buffer solution. Thus, in cases where the nucleic acid sample comprises double stranded DNA in a buffer solution, the denaturing electrical potential should be strong enough to apply a stretching force of at least 65 pN along the DNA strands.

The vcPCR methods of the present invention may be used to effect rapid denaturation of double stranded nucleic acids without the need for the use of chemical initiators, accelerators or modifiers of the type described in U.S. Pat. No. 6,365,400 (Stanley). Accordingly, it is to be appreciated that any of the examples or embodiments described herein may, in at least some embodiments, be carried out in the absence of substantial amounts of chemical initiators or accelerator compositions of the type described in U.S. Pat. No. 6,365,400 (Stanley).

Methods for Performing vcPCR

A. Bridge Amplification

Figure 1:
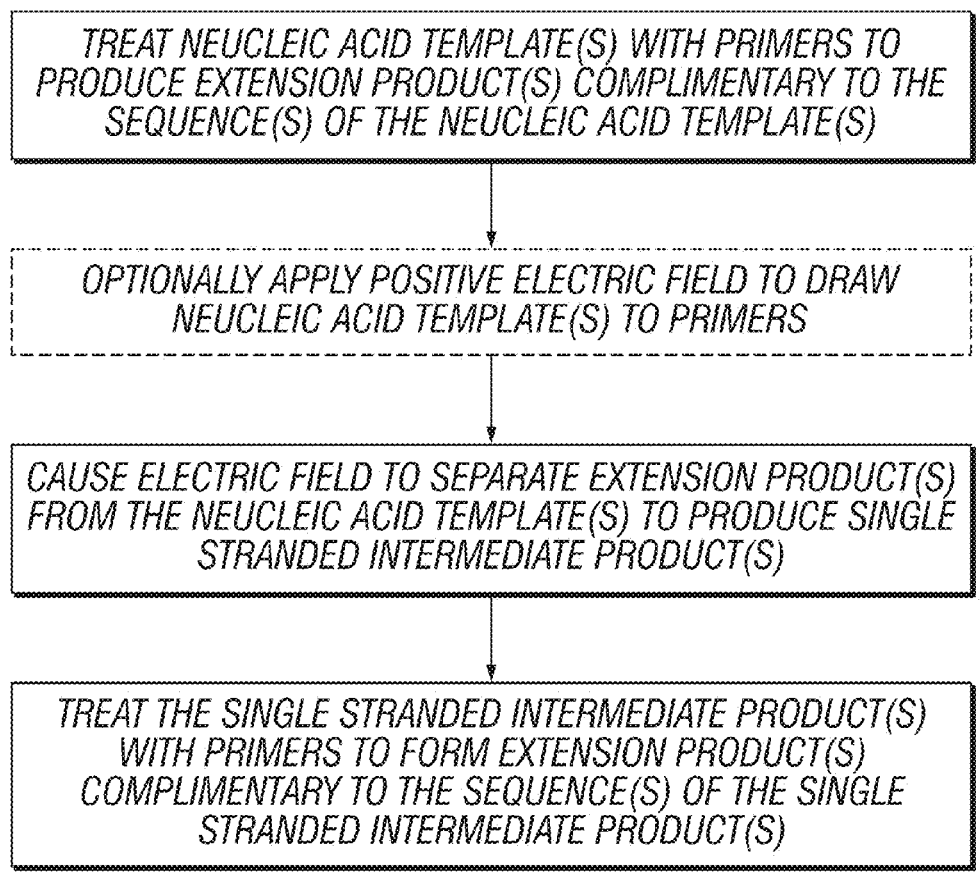
FIG. 1 is a flow diagram showing a general method for nucleic acid amplification in accordance with the present invention.
Figure 2:
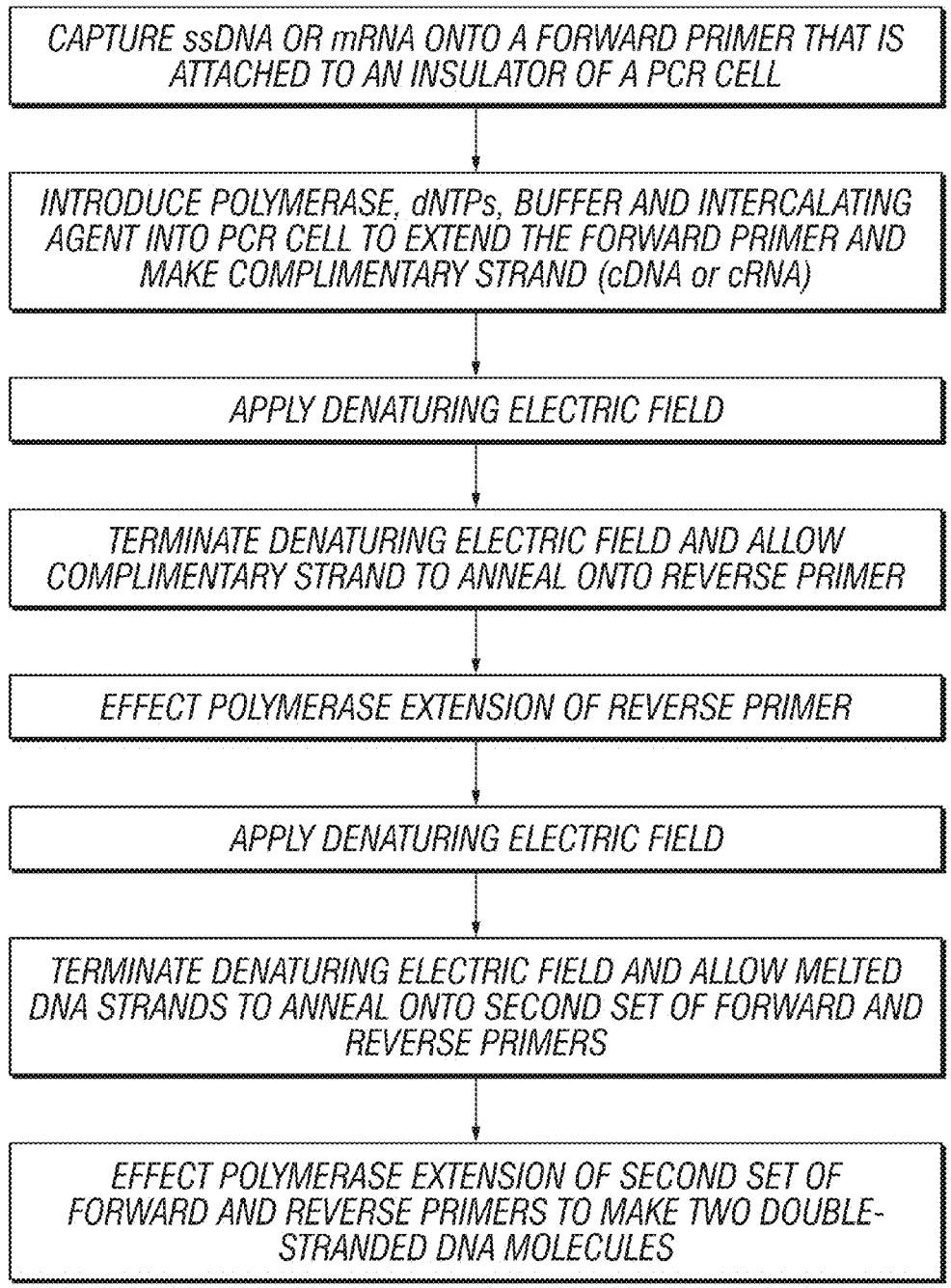
FIG. 2 is a flow diagram showing one example of a method for DNA analysis in accordance with the present invention.
Figure 3:
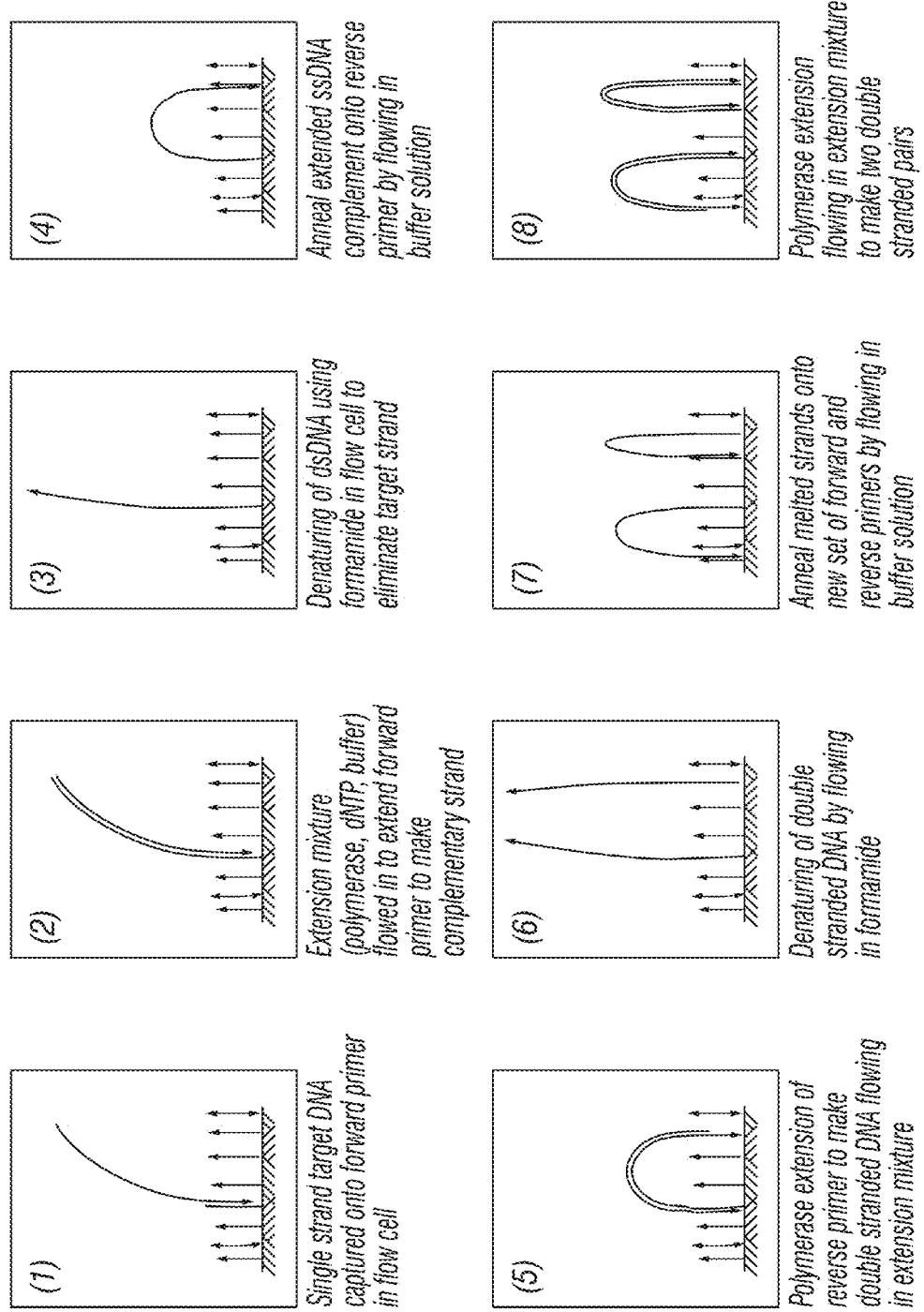
FIG. 3 (Panels 1 through 8) are schematic diagrams showing a prior art method for DNA analysis by solid state bridge amplification in a flow cell.

In vcPCR Bridge Amplification, both forward and reverse primers are randomly attached at their 5' end onto a solid substrate. Following PCR amplification, both forward and reverse strands of the amplified templates section remain bound at their 5' ends in a double stranded "bridge" arrangement (FIG. 3).

Figure 4:
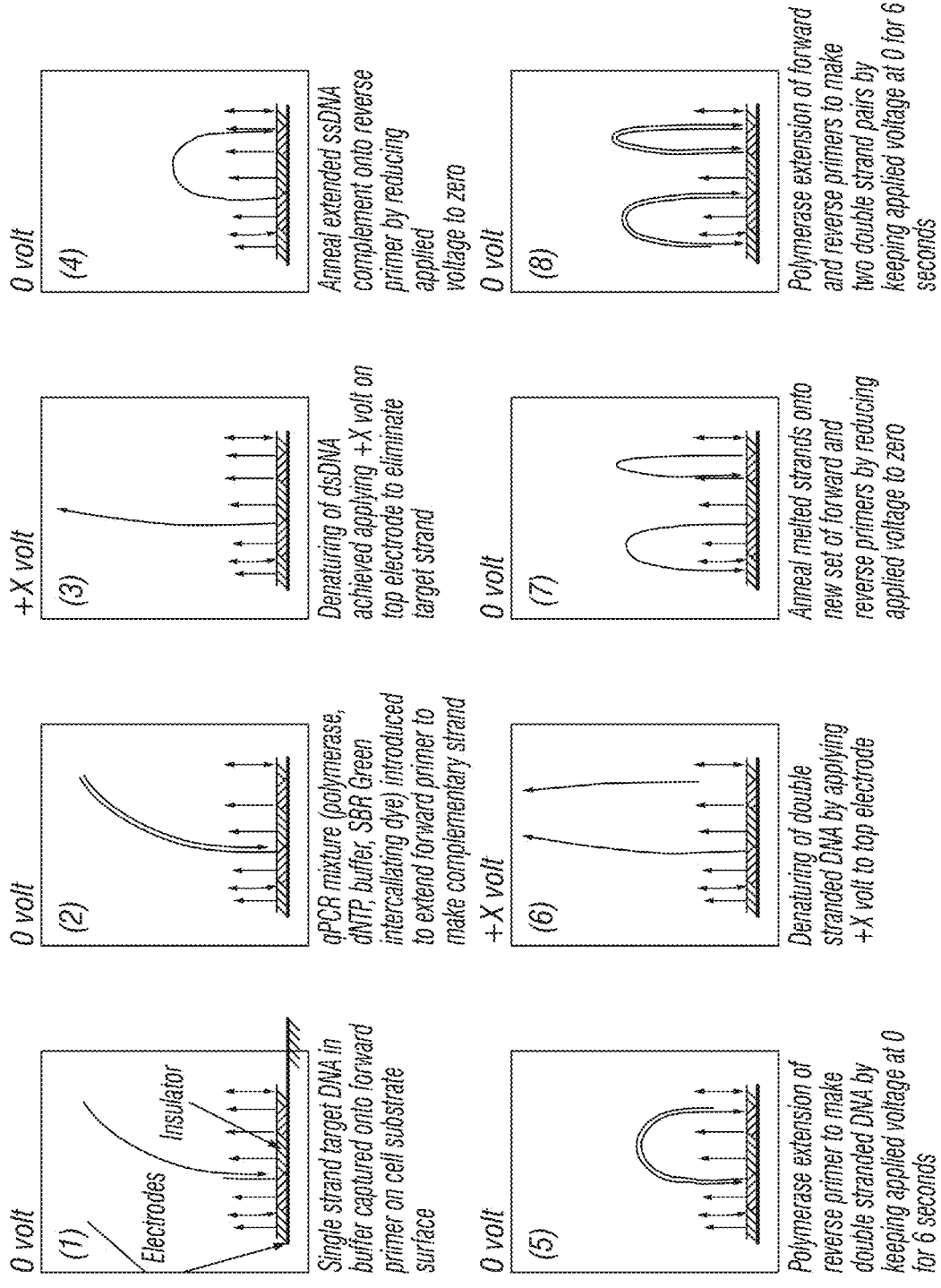
FIG. 4 (Panels 1 through 8) are schematic diagrams showing steps in a non-thermal method for DNA analysis by solid state bridge amplification in a flow cell in accordance with the present invention.

FIG. 4 shows a vcPCR scheme for bridge amplification. The steps for vcPCR cycling are illustrated in FIG. 4 and are as follows:
(1) Capture ssDNA from buffer solution onto the forward primer attached on the insulator oxide (typically Silicon Dioxide) film on the PCR cell substrate (typically Silicon);
(2) Introduce qPCR master mix (Polymerase, dNTP's, buffer, SYBR Green intercalating dye) into PCR cell to extend forward primer and make complementary strand (typically 6 seconds or shorter depending on the polymerase used).
(3) Apply a positive voltage on the upper electrode to create a sufficiently high E-field (in excess of $10^6$ v/m for a 100 base DNA strand) to denature dsDNA and eliminate the target strand. In our experiments, we applied a field of $4 \times 10^7$ v/m.
(4) Anneal extended ssDNA complement onto reverse primer by reducing the applied voltage to zero.
(5) Polymerase extension of reverse primer to make dsDNA by keeping applied voltage at zero for 6 seconds-100 base amplicon will be extended in 6 seconds for Taq polymerase at a polymerase extension speed of 1000 bases per minute. Depending on the specific polymerase used, this speed can be increased by 50×.
(6) Apply a positive voltage on the upper electrode (as in step 3) to denature dsDNA.
(7) Anneal melted strands onto new set of forward and reverse primers by reducing applied voltage to zero.
(8) Extend forward and reverse primers to make two double stranded DNA's by keeping applied voltage at zero for 6 seconds (for a 100 base amplicon).
(9) Go to step (6) to denature the two dsDNA's and repeat steps (6) to (8) for each PCR cycle.

The total time for 40 PCR cycles is approximately 240 seconds or 4 minutes. Amplification after each cycle can be quantified by measuring the fluorescence level from each cell after excitation with a suitable pump light source as in conventional q PCR.

B. Solid Phase Amplification with a Single Forward Primer

Figure 5:
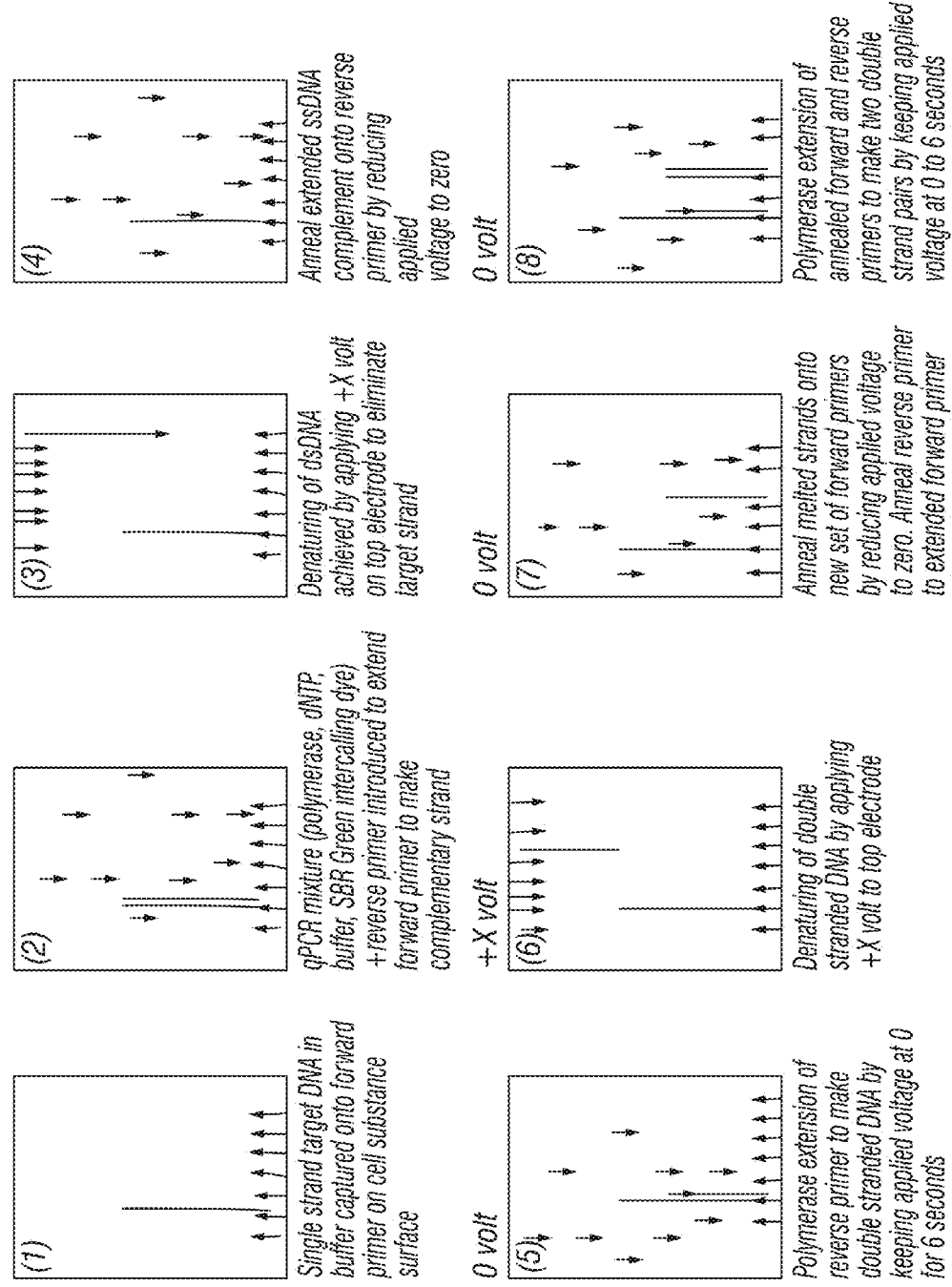
FIG. 5 (Panels 1 through 8) are schematic diagrams showing steps in a non-thermal method for DNA analysis by solid phase amplification with a single forward primer in accordance with the present invention.

This scheme is essentially similar to scheme (a) except that only the forward primer is attached to the solid surface—just like in emulsion bead PCR; the reverse primer is in the PCR master mix. This amplification scheme for vcPCR cycling is illustrated in FIG. 5. This method comprises the following steps:
(1) Single strand target DNA in buffer captured onto forward primer on cell substrate surface.
(2) qPCR mixture (polymerase, dNTP, buffer, SBR Green intercalating dye)+reverse primer introduced to extend forward primer to make complementary strand.
(3) Denaturing of dsDNA achieved by applying +X volt on first (top) electrode to eliminate target strand.
(4) Anneal extended ssDNA complement onto reverse primer by reducing applied voltage to zero.
(5) Polymerase extension of reverse primer to make double stranded DNA by keeping
(6) Denaturing of double stranded DNA by applying +X volt to first (top) electrode.
(7) Anneal melted strands onto new set of forward primers by reducing applied voltage to zero. Anneal reverse primer to extended forward primer.
(8) Polymerase extension of annealed forward and reverse primers to make two double strand pairs by keeping applied voltage at 0 for 6 seconds.

Devices for Performing vcPCR

Figure 6:
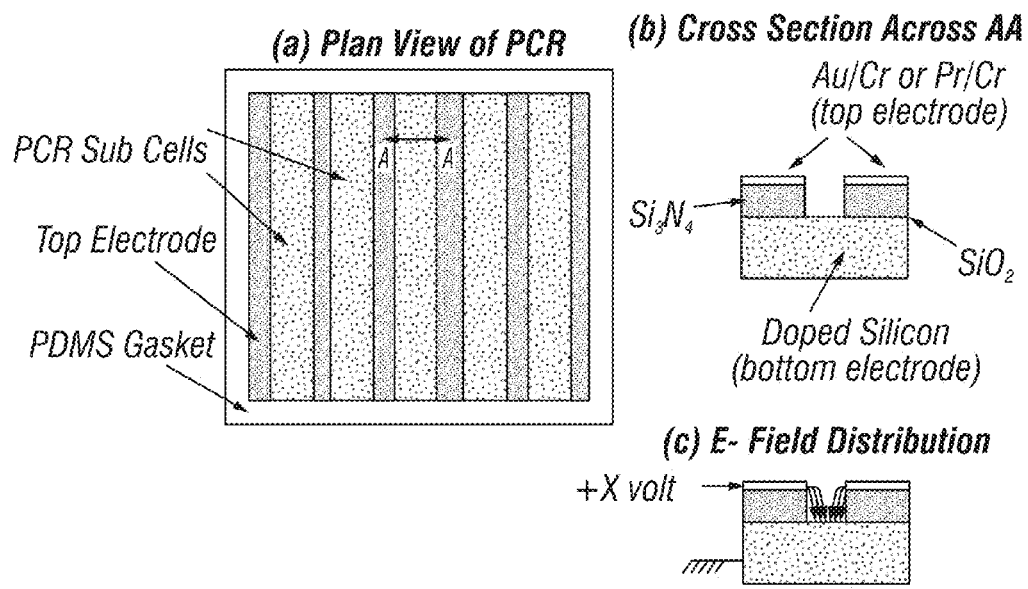
FIG. 6 shows various views of a voltage cycled PCR device of the present invention having rectangular sample wells.
Figure 7:
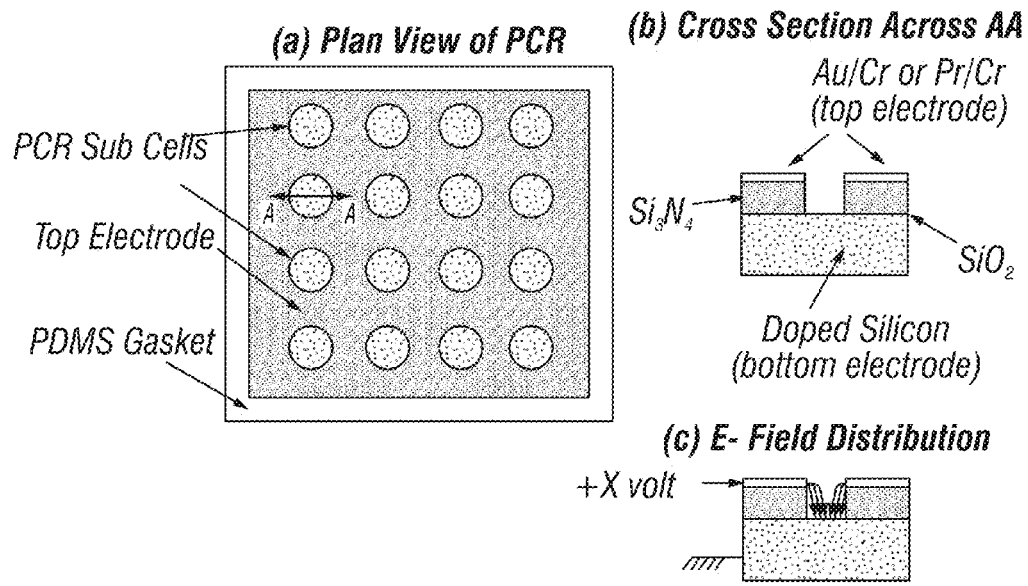
FIG. 7 shows various views of a voltage cycled PCR device of the present invention having round sample wells.
Figure 8:
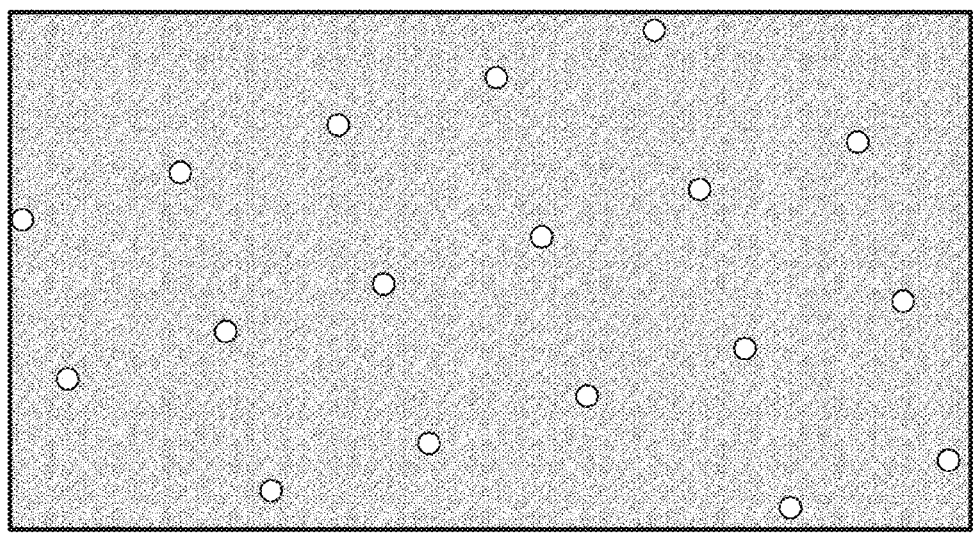
FIG. 8 shows fluorescence from SYBR Green intercalating dye after 40 cycles of voltage cycled PCR in accordance with the present invention, thus indicating that bridge amplification has taken place.

FIG. 6 shows an example of a vcPCR device having rectangular wells and FIG. 7 shows an example of a vcPCR device having cylindrical wells. It is to be appreciated, however, that various other shapes of cells other than rectangular or cylindrical may be used. Each of these devices generally comprises a) a base electrode member, b) a gasket member that is disposed on top of the base electrode member and has openings formed in it to define one or more the sample wells and c) a top electrode member disposed on top of the gasket member. As shown the gasket member is positioned on the base electrode member such that at least part of the floor of each sample well is formed by the base electrode member. Voltage cycling apparatus may be connected to one or both of said base and top electrode members to intermittently create an electrical field to denature nucleic acid contained within each of the sample well(s). In these examples, the voltage cycling apparatus is operative to cerate a denaturing electrical potential is in excess of $10^6$ v/m, for example approximately $4 \times 10^7$ μm, within each of the sample well(s).

The base electrode member may comprise an electrically conductive layer having an insulating film disposed thereon. For example, the electrically conductive layer may comprise doped silicon or another suitable electrically conductive material and the insulating film may comprise silicon dioxide or another suitable insulating film material.

The gasket member may comprise a substantially non-porous electrically insulating material such as, for example, a glass, silicon polymer, silicon nitride or Polydimethylsiloxane (PDMS).

The top electrode member may comprises a layer of metal, for example an Au/Cr or Au/Pt film.

In some embodiments, as described above, an oligonucleotide primer may be attached to a substrate that comprises or is located in proximity to the base electrode member. For example, the 5' end of an oligonucleotide primer may be attached to an insulating film that is attached to the base electrode member.

The following are typical, but non-limiting, dimensions for the vcPCR devices of the present invention:
Electrodes: Cr 10 nm, Au 100 nm or Cr 10 nm, Pt 100 nm
Films: $SiO_2$ nm, $ShN_4$ 500 nm
Diameter (if cylindrical) or width (if rectangular) of the sample wells: 1 to 3 μm
PDMS gasket dimensions: Approximately 2 mm×2 mm-3 mm×3 mm range.

Typically, in these exemplary devices, the applied voltage X is in the range of 10-20 volts, but any workable voltage capable of causing the described effects may be used.

The following is a calculation of expected electrical potential and stretching force on an attached DNA double strand or X=10 v, assuming sub-wells are filled with buffer (E=36)
Electrical potential at the surface of $SiO_2$ (E=4), thickness=0.02 μm is
E=10V/(0.5+0.02×36/4) μm or $1.47 \times 10^7$ V/m Force on a 100 base long ds DNA molecule attached to the SiO$_2$ surface is F=100 q E where q is charge of a single base ~e the electronic charge so F=882 pN or more than 10× the melting threshold force published in the literature 1.

FIG. 6 shows fluorescence from 1 μm cylindrical wells after 40 cycles of vcPCR.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless otherwise specified of if to do so would render the embodiment or example unsuitable for its intended use. Also, where the steps of a method or process have been described or listed in a particular order, the order of such steps may be changed unless otherwise specified or unless doing so would render the method or process unworkable for its intended purpose. All reasonable additions, deletions, modifications and alterations are to be considered equivalents of the described examples and embodiments and are to be included within the scope of the following claims.

What is claimed is:

1. A method for separating the strands of a double-stranded nucleic acid or double-stranded nucleic acid/primer extension product, said method comprising the step of:
    causing the double-stranded nucleic acid or double-stranded nucleic acid/primer extension product and a solution to be present within a cell in the substantial absence of any initiator or promoter substance selected from the group of: lithium ions, methyl viologen, benzyl viologen, neutral red, phenosafranin and salts thereof, wherein the cell has first and second electrodes and wherein one of the first and second electrodes is in direct contact with the solution and the other of the first and second electrodes is in direct contact with the solution and the other of the first and second electrodes is separated from the solution by an insulator;
    applying an electrical potential in excess of $10^6$ v/m between the first and second electrodes thereby creating a stretching force of at least 65 pN which results in non-thermal separation of strands of the double-stranded nucleic acid or double-stranded nucleic acid/primer extension product.

2. A method for amplifying a target nucleic acid sequence contained in a sample that consists of or contains one or more nucleic acid(s), said method comprising the steps of:
    a) treating, the sample with primers for the target sequence under conditions that produce a primer extension product that is complementary to the target nucleic acid sequence;
    b) performing the method of claim 1 to separate the primer extension product from the nucleic acid on which it was synthesized, thereby producing a single-stranded intermediate product; and
    c) treating the single-stranded intermediate product with the primers under annealing conditions to cause a further primer extension product to be produced.

3. A method according to claim 2 wherein an electrical potential is also applied during Step a to draw the target sequence to the primers.

4. A method according to claim 2 wherein Step b comprises exposing a reaction mixture that contains the solution and at least i) a nucleic acid or a mixture of nucleic acids, ii) the primers, iii) a polymerase and iv) extension subunits, to the electrical potential.

5. A method according to claim 4 wherein Step c comprises:
    terminating exposure to the electrical potential for a second period of time under conditions that result in annealing of the primers to the single-stranded molecules; and
    allowing or causing polymerase-mediated production of the further extension product.

6. A method according to claim 4 wherein:
    the nucleic acid or mixture of nucleic acids comprises DNA;
    the polymerase comprises at least one DNA polymerase; and
    the extension subunits comprise at least one deoxyribonucleotide triphosphate.

7. A method according to claim 6 wherein the deoxyribonucleotide triphosphate is/are selected from dATP, dTTP, dCTP and dGTP.

8. A method according to claim 2 wherein at least one of the primers is attached to the insulator.

9. A method according to claim 8 wherein 5' end(s) of the primer or primers is/are attached to the insulator.

10. A method according to any of claims 2-9 wherein Steps b and c are performed at substantially the same temperature.

11. A method according to claim 10 wherein Steps b and c are carried out at ambient temperature.

12. A method according to claim 10 wherein Steps b and c are carried out at a temperature above ambient temperature.

13. A method according to claim 12 wherein the temperature above ambient temperature is selected to optimize specificity of the amplified product during annealing.

14. A method according to claim 5 further comprising raising the temperature during formation of the primer extension product.

* * * * *